United States Patent [19]

Phillips et al.

[11] Patent Number: 5,143,713

[45] Date of Patent: Sep. 1, 1992

[54] 99MTC LABELED LIPOSOMES

[75] Inventors: William T. Phillips; Robert W. Klipper, both of San Antonio, Tex.; James H. Timmons, Tacoma, Wash.; Alan S. Rudolph, Bowie, Md.

[73] Assignees: Board of Regents, The University of Texas System, Austin, Tex.; The United States of America as represented by the Secretary of the Navy, Washington, D.C.

[21] Appl. No.: 610,204

[22] Filed: Nov. 5, 1990

Related U.S. Application Data

[63] Continuation-in-part of Ser. No. 530,847, May 30, 1990.

[51] Int. Cl.$^5$ .................. A61K 43/00; A61K 49/02; A61K 9/127
[52] U.S. Cl. ......................... 424/1.1; 534/10; 534/14; 424/450; 428/402.2; 435/7.24
[58] Field of Search .................. 424/1.1, 450; 534/10, 534/14

[56] References Cited

U.S. PATENT DOCUMENTS

| | | | |
|---|---|---|---|
| 4,335,095 | 6/1982 | Kelly | 424/9 |
| 4,452,774 | 6/1984 | Jones et al. | 424/1.1 |
| 4,615,876 | 10/1986 | Troutner et al. | 424/1.1 |
| 4,707,544 | 11/1987 | Jones et al. | 424/1.1 X |
| 4,735,793 | 4/1988 | Jones et al. | 424/1.1 |
| 4,789,736 | 12/1988 | Canning et al. | 424/1.1 X |
| 4,826,961 | 4/1989 | Jones et al. | 424/1.1 X |
| 4,911,929 | 3/1990 | Farmer et al. | 424/450 |
| 4,925,650 | 11/1988 | Nosco et al. | 424/1.1 |
| 4,935,223 | 6/1990 | Phillips | 424/1.1 |
| 4,938,947 | 7/1990 | Nicolau et al. | 424/1.1 |
| 5,019,369 | 5/1991 | Presant et al. | 424/1.1 |
| 5,049,391 | 9/1991 | Suzuki et al. | 424/450 |

OTHER PUBLICATIONS

Atsushi Takeda et al., "Intensification of Tumor Affinity of $^{99m}$TC-DL-Homocysteine by Cooperative Use of SH-containing Compounds", Nucl. Med. Biol., vol. 16, No. 6, pp. 581-585, 1989.
Claire De Labriolle-Vaylet et al., "Morphological and Functional Status of Leukocytes Labelled with $^{99m}$ Technetium HMPAO", Radiolabelled Cellular Blood Elements, pp. 119-129.
Laurence Guilloteau et al., "Recruitment of $^{99m}$-Technetium- or 111-Indium-Labelled Polymorphonuclear Leucocytes in Experimentally Induced Polygranulomas in Lambs", J. of Leukocyte Bio., vol. 48, pp. 343-352, (1990).
Dialog Search Report.
Karl J. Hwang, "Liposome Pharmacokinetics," In: Liposomes from Biophysics to Therapeutics (M. J. Ostro, Ed.), pp. 109-156 (Marcel Dekker, Inc.) New York 1987.
Caride and Sostman, "Methodological Considerations for the Use of Liposomes in Diagnostic Imaging," Liposome Technology, vol. II:107-124 (1984).
Barratt et al., "The Labeling of Liposomal Membranes with Radioactive Technetium," Liposome Technology vol. II:93-106 (1984).
Beaumier and Hwang, "An Efficient Method for Loading Indium-111 into Liposomes Using Acetylacetone," J. of Nucl. Med. 23(9):810-815.

(List continued on next page.)

Primary Examiner—Richard D. Lovering
Assistant Examiner—John M. Covert
Attorney, Agent, or Firm—Arnold, White & Durkee

[57] ABSTRACT

The invention relates to the efficient preparation of radionuclide labeled liposomes and radionuclide-labeled liposome-encapsulated protein. In particular, a $^{99m}$Tc carrier is used to label preformed liposomes or liposome-encapsulated hemoglobin. $^{99m}$Tc-labeled liposomes and liposome-encapsulated $^{99m}$Tc labeled hemoglobin are highly stable in vitro and in vivo and are suitable for a variety of clinical uses, including biodistribution imaging studies. The invention also relates to a method of labeling neutrophils using $^{99m}$technetium-labeled liposomes or liposome-encapsulated hemoglobin. A kit method useful for the convenient preparation of $^{99m}$Tc-labeled liposomes or liposome-encapsulated hemoglobin for clinical use is also disclosed.

31 Claims, 8 Drawing Sheets

OTHER PUBLICATIONS

Caride, Vincente J. "Technical and Biological Considerations on the Use of Radio-labeled Liposomes for Diagnostic Imaging," Nucl. Med. Biol. 17(1):35–39 (1990).

Turner et al., "In-111-labeled liposomes: Dosimetry and Tumor Depiction," Radiology 166:761–765 (1988).

Proffitt et al., "Tumor-Imaging Potential of Liposomes Loaded with In-111-NTA: Biodistribution in Mice," J. of Nucl. Med. 24(1):45–51 (1983).

Hnatowich et al., "Labeling of Preformed Liposomes with Ga-67 and Tc-99m by Chelation," J. of Nucl. Med. 22(9):810–814 (1981).

Love et al., "Effect of liposome surface charge on the stability of technetium ($^{99m}$Tc) radiolabelled liposomes," J. Microencapsulation 6(1):105–113 (1989).

O'Sullivan et al., "Inflammatory joint disease: a comparison of liposome scanning, bone scanning, and radiography," Annals of the Rheumatic Diseases 47:485–491 (1988).

Williams et al., "Synovial accumulation of technetium labelled liposomes in rheumatoid arthritis," Annals of the Rheumatic Diseases 46:314–318 (1987).

Morgan et al., "Localisation of experimental staphylococcal abscesses by $^{99m}$Tc-technetium-labelled liposomes," J. Med. Microbiol. 14:213–217 (1981).

Eisenhut, M. "Radiopharmaka für die szintigraphische Tumordiagnostik," supplied by National Library of Medicine.

Osborne et al., "Radionuclide-Labelled Liposomes—A New Lymph Node Imaging Agent," Int'l J. of Nucl. Med. and Biol. 6:75–83 (1979).

Yu Bao-fa et al., "A New Lymph Node Imaging Agent-$^{99m}$Tc-polyphase Liposome Oleatis ($^{99m}$Tc-plo)," J. Oncol. (China) 10:270–273 (1988).

Farr et al., "99m-Technetium as a marker of liposomal deposition and clearance in the human lung," Int'l J. of Pharmaceutics 26:303–316 (1985).

Palmer et al., "The Mechanism of Liposome Accumulation in Infarction," Biochemica et Biophysica Acta 797:363–368 (1984).

Callahan et al., "A Modified Method for the In Vivo Labeling of Red Blood Cells with Tc-99m: Concise Communication," J. Nucl. Med. 23:315–318 (1982).

Dewanjee, M. K. "Binding of $^{99m}$Tc Ion to Hemoglobin" J. of Nuclear Medicine 15(8):703–706 (1974).

Deliconstantinos et al., "Interaction of $^{99m}$Tc-Labeled Liposomes With Walker Tumor Cell In Vitro. Liposome-Mediated Introduction of Thalblastine Into Resistant Walker Tumor Cells" Gen. Pharmac. 14(4):407–411 (1983).

Nakamura et al., "The behavior of $^{99m}$Tc-hexamethylpropyleneamineoxime ($^{99m}$Tc-HMPAO) in blood and brain" Eur. J. Nucl. Med. 15:100–107 (1989).

Unger et al., "Gadolinium-DTPA Liposomes as a Potential MRI Contrast Agent Work in Progress" Investigative Radiology 23(12):928–932 (1988).

Seltzer, S. E. "The Role of Liposomes in Diagnostic Imaging" Radiology 171(1):19–21 (1989).

Article in Radiology Today, Mar. 1989 "Indium-labeled liposomes effectively target secondary tumors" p. 3.

Article by Lang, Letters to the Editor, J. Nucl. Med., 31(6):1115 (1990).

Article by Ballinger, Letters to the Editor, J. Nucl. Med., 31(6):1116 (1990).

Article by Ballinger et al., "Technetium-99m HM-PAO Stereoisomers: Differences in Interaction with Glutathione", J. Nucl. Med., 29(12):1998–2000 (1988).

30 MIN IMAGE

Fig. 12A

90 MIN IMAGE

Fig. 12B

20 HOUR IMAGE (UPPER)

Fig. 12C

20 HOUR IMAGE (LOWER)

Fig. 12D

99MTC LABELED LIPOSOMES

The U.S. Government may have certain rights in the present invention pursuant to the terms of Grant No. N 00014-89-K-0077 awarded by the Office of Naval Research.

This is a continuation-in-part of U.S. patent application Ser. No. 07/530,847, filed May 30, 1990.

BACKGROUND OF THE INVENTION

1. Field of the Invention

The invention relates to a rapid and highly efficient method of labeling liposomes and liposome-encapsulated protein. In particular, the method relates to radionuclide labeling of preformed liposomes with or without encapsulated protein by means of a radionuclide carrier characterized as being membrane diffusible.

Table 1 is a list of abbreviations used.

TABLE 1

| | |
|---|---|
| cpm | counts per minute |
| DTPA | diethylenetriaminepenta-acetic acid |
| GBq | gigabequerels |
| HMPAO | hexamethylenepropylene amine oxime |
| LEH | liposome-encapsulated hemoglobin |
| PBS | phosphate buffered saline |
| PYP | pyrophosphate |
| Tc | Technetium |
| LUV | large unilamellar vesicles |

2. Description of Related Art

Liposomes are of considerable interest because of their value as carriers for diagnostic agents, particularly radiopharmaceuticals for tracer and imaging studies. Successful biodistribution studies, for example, require attachment of a radiolabel to the liposome. Unfortunately, the entrapment of water soluble radionuclides within the liposome is relatively inefficient. Another major problem in using liposomes is their leakiness, resulting in limited usefulness for many applications (Hwang, K. J., in Liposomes from Biophysics to Therapeutics, M. J. Ostru, Ed., Marcel Dekker, N.Y., 1987).

Radioactive markers have been widely used as a non-invasive method for studying the distribution of drugs in vivo. The use of gamma emitting radioisotopes is particularly advantageous because, unlike beta-emitters, they can easily be counted in a scintillation well counter and do not require tissue homogenization prior to counting. In addition, gamma-emitters can be imaged with nuclear gamma cameras. With this type of imaging, the dynamic biodistribution can be followed non-invasively using consecutive one minute computer acquired scintigraphic images which are analyzed to calculate organ biodistribution curves.

The most common radiolabel used in diagnostic radiopharmaceuticals today is $^{99m}$Tc. This radionuclide is produced from the beta decay of $^{99}$molybdenum and has a half-life of 6 hours. It is widely available from a generator system at low cost and its relatively short half-life provides for safer and more convenient handling than other available radionuclides. Its gamma emission is in the range of 140 Kev which is an ideal range for producing high resolution images (Caride, V. J. and Sostman, H. D. in Liposome Technology, Vol. II, G. Gregoriadis, Ed., CRC Press, Boca Raton, 1984). Heptavalent $^{99m}$TcO$_4^-$ is produced from the generator and since it is relatively unreactive, must be reduced to a lower oxidation state before use as a radiopharmaceutical. Stannous chloride is the most commonly used reducing agent (Barratt, G. M., Tuzel, N. S. and Ryman, B. E. in Liposome Technology, Vol. II, G. Gregoriadis, Ed., CRC Press, Boca Raton, 1984).

Radiolabeled complexes have been employed as a means for labeling liposomes. Isonitrile radionuclide complexes of Tc and other gamma-emitters appear to have use for labeling vesicles with lipid membranes, including red blood cells (U.S. Pat. No. 4,452,774, Jones et al., Jun. 5, 1984). Propylene amine oxime complexes with $^{99m}$Tc are stable neutral lipophilic complexes which have been approved for radioimaging in vivo as an adjunct in the detection of altered regional cerebral perfusion (Ceretec TM). These complexes which diffuse across cellular walls have been shown to localize in red blood cells, although radioactivity is readily washed from the cells. (U.S. Pat. No. 4,789,736, Canning et al., Dec. 6, 1988 and U.S. Pat. No. 4,615,876, Troutner et al., Oct. 7, 1986). Furthermore, the usefulness of these complexes is limited because the complexes are not stable. Ceretec TM, for example, has a useful life of approximately 30 minutes.

The radionuclide of $^{111}$indium ($^{111}$In) has found some use as an imaging agent. Multilamellar lipid vesicles labeled with $^{111}$In using 8-hydroxyquinoline showed a labeling efficiency of 30% (Caride, V. J. and Sostman, H. D. in Liposome Technology, Vol. II, G. Gregoriadis, Ed., CRC Press, Boca Raton, 1984). Higher labeling efficiencies have been shown for loading $^{111}$In into the aqueous compartment of liposomes. Acetylacetone, a water soluble lipophilic chelator, can be complexed with $^{111}$In. This is then mixed with liposome-encapsulated nitrilotriacetic acid with subsequent formation of labeled nitrilotriacetic acid. The resulting labeled liposomes are unstable unless excess acetylacetone is removed by an ion exchange process (Beaumier, P. L. and Hwang, K. J., J. Nucl. Med., 23, 810–815 (1982)).

In general, labeling efficiency of 50–70% for $^{99m}$Tc has been reported for multilamellar vesicles and 4–20% for small unilamellar vesicles when using stannous chloride to reduce the pertechnetate. A persistent problem in all these methods is the removal of excess reducing agent as well as elimination of free pertechnetate. Separation can be done by gel filtration or dialysis, but there is often formation of a $^{99m}$Tc-tin chloride colloid which is not readily distinguishable or separable from the liposomes (Barratt, G. M., Tuzel, N. S. and Ryman, B. E. in Liposome Technology, Vol. II, G. Gregoriadis, Ed., CRC Press, Boca Raton, 1984). This confounds the results of biodistribution studies since interpretation may be subject to altered uptake influenced by the labeled colloidal tin.

Attempts at labeling liposomes with imaging radiotracers have produced variable results (Barratt, G. M., Tuzel, N. S. and Ruman, B. E. in Liposome Technology, Vol. II, G. Gregoriadis, Ed., CRC Press, Boca Raton, 1984; Caride, V. J. and Sostman, H. D. in Lipid Technology, Vol. II, G. Gregoriadis, Ed., CRC Press, Boca Raton, 1984; Caride, V. J., Nucl. Med. Biol., 17, 35–39 (1990); Hwang, K. J. in Liposomes from Biophysics to Therapeutics, M. J. Ostro, Ed., Marcel Dekker, Inc., N.Y., 1987). Many radioisotope labels weakly bind to liposomes resulting in inaccurate biodistribution data. A more efficient imaging label procedure uses $^{111}$indium chloride ($^{111}$InCl) and nitrilotriacetic acid, a metal chelator (Beaumier, P. L. and Hwang, K. J., J. Nucl. Med., 23, 810–815 (1982); Turner, A. F., Presant, C. A., Proffitt, R. T., Williams, L. E., Winsor, D. W., Werner, J. L., Radiology, 166, 761-765 (1988); Proffitt, R. T., Williams, L. E., Presant, C. A., Tin, G. W., Uliana, J. A., Gamble, R. C. and Baldeschwieler, J. D., J. Nucl. Med., 24, 45-51 (1983). The nitrilotriacetic acid is incorporated into the liposome during the manufacturing process. The preformed liposomes are then incubated for 30 minutes with $^{111}$InCl. Although the $^{111}$InCl nitrilotriacetic acid labeling method has proven to be effective and the label tightly attached to the liposome, a heating step (60° C.) is required, which adds to the time and inconvenience involved in the preparation. In a clinical situation convenience and speed are important. A further consideration is the expense of the $^{111}$In radionuclide. The present cost of $^{111}$In is approximately $135/mCi while cost of $^{99m}$Tc, a superior imaging agent, is $0.35/mCi. This difference is highly significant in determining cost of imaging procedures to the patient and in a decision by the health provider to offer such services.

Other labeling carriers have been tried. Small amounts of octadecylamine-DTPA in liposomes have been shown to rapidly label the liposomes with $^{67}$Ga or $^{99m}$Tc by chelation with efficient labeling, but over 30% of the label is lost after a 2 hour incubation in plasma (Hnatowich, D. J., Friedman, B., Clancy, and Novak, M. J. Nucl. Med., 22, 810-814 (1981).

The reasons for instability of $^{99m}$Tc labeled liposomes are not well understood, although instability may be related to the liposome surface charge. Recent work has shown that the in vitro methods currently used to assess the stability of labeled liposomes do not predict isotope stability in vivo, and that the nature of the binding between the isotope and the liposome surface is important in regulating in vivo isotope stability (Love, W. G., Amos, N., Williams, B. D., and Kellaway, I. W., J. Microencapsulation, 6, 103-113 (1989)). The result is that even when labeling methods appeared to be highly efficient, and little instability was demonstrated in plasma or serum, significant loss of label could occur when the labeled liposomes were introduced into an animal or human.

Despite attempts to develop stable $^{99m}$Tc-labeled liposomes, there has been little success. In a thoroughly detailed review of liposomal labeling with radioactive technetium, Barratt et al. noted that technetium labeling techniques vary widely in efficiency. Moreover, stability is generally recognized to be poor, especially in vivo. Most methods of labeling liposomes with $^{99m}$Tc encapsulate the $^{99m}$Tc during liposome manufacture. However, these encapsulation methods do not solve the problem of in vivo dissociation of $^{99m}$Tc from the liposome. The dissociated $^{99m}$Tc is usually visualized in the kidneys and bladder. These problems clearly illustrate that development of a reliable method to load high levels of $^{99m}$Tc into liposomes without in vivo dissociation would be beneficial in view of the many clinical uses for radiolabeled liposomes (Hwang, K. J. in Liposomes from Biophysics to Therapeutics, M. J. Ostro, Ed., Marcel Dekker, N.Y., 1987).

There are numerous clinical applications for $^{99m}$Tc-liposomes. Comparison studies of liposome scanning, bone scanning and radiography have been performed in inflammatory joint disease. Liposome scans have been shown to be positive only in clinically active inflammatory disease. The method has also been able to discriminate between different grades of joint tenderness, in contrast to bone scans (O'Sullivan, M. M., Powell, N., French, A. P., Williams, K. E., Morgan, J. R., and Williams, B. D., Ann. Rheum. Dis., 47, 485-491, 1988; Williams, B. D., O'Sullivan, M. M., Saggu, G. S., et al., Ann. Rheum. Dis. (UK), 46, 314-318 (1987)). Other studies include the localization of abscesses (Morgan, J. R., Williams, K. E., Davies, R. L., et al., J. Med. Microbiol., 14, 213-217 (1981); tumor scanning (Eisenhut, M., Therapiewoche (West Germany) 30, 3319-3325 (1980); lymph node imaging (Osborne, M. P., Richardson, V. J., Jeyasingh, K., Ryman, B. E., Int. J. Nucl. Med. Biol. (England) 6, 75-83 (1979; Yu, B., Chin. J. Oncol. (China) 10, 270-273 (1988)); clearance in the human lung (Farr, S. J., Kellaway, I. W., Parry-Jones, D. R., Woolfrey, S. G., Int. J. Pharm. (Netherlands) 26, 303-316 (1985)); and infarction (Palmer, T. N. Caride, V. J., Caldecourt, M. A., Twickler, J., and Abdullah, V., Biochim. Biophys. Acta 797, 363-368 (1984)).

Other potential uses of a liposome label include cardiac gated blood pool angiography and gastrointestinal bleeding detection. The most commonly used process known as the modified in vivo technique is fairly lengthy and requires 2-3 injections into the patient. For red blood cell labeling, the patient is injected with 1-2 mg of stannous PYP (Callahan, R. J., et al., J. Nuclear Medicine 23, 315-318 (1982)). Fifteen minutes later a blood sample is withdrawn and incubated with $^{99m}$TcO$_4^-$ (free pertechnetate). The patient is then reinjected with the radiolabeled blood, the whole procedure requiring up to 1 hour. The major disadvantage of this technique is that the label is often poor and free pertechnetate is taken up in the stomach, resulting in intestinal contamination and making the results difficult to interpret. A rapid labeling technique would very likely alleviate this major problem, allowing improved cardiac and gastrointestinal bleeding detection imaging.

There is a distinct need for radiopharmaceutical materials that can be broadly applied to clinical applications and to biodistribution and bioimaging studies. $^{99m}$Tc labeled liposomes would appear to be an ideal reagent but present methods of labeling liposomes with $^{99m}$Tc are generally inefficient. A far greater problem is the lack of in vivo stability of $^{99m}$Tc labeled liposomes, thereby limiting their use and creating uncertainty in interpretation of results.

The present invention is the surprising discovery that incubation of encapsulated reducing agent with liposomes, radionuclide labeled liposomes having high in vivo stability can be readily and efficiently prepared. The liposomes, preferably labeled with $^{99m}$Tc, are useful in a wide range of clinical applications related to biodistribution and imaging. Labeled liposome-encapsulated protein may also be prepared by this method and has also been shown to have high stability in vivo.

SUMMARY OF THE INVENTION

Stable $^{99m}$Tc-labeled liposomes and $^{99m}$Tc labeled liposome-encapsulated protein and their novel method of preparation are the subject of the present invention. The method of preparation results in over 95% labeling efficiency and produces labeled liposomes that are surprisingly stable in vivo for relatively long periods of time. The labeled liposomes are excellent imaging agents.

Labeled liposomes (LL) may be prepared by incubating liposomes with a label, generally a radionuclide, in the form of a complex which acts as a carrier for the label. It has been found that labeling is surprisingly efficient when the incubating is performed in the presence of an antioxidant compound. The antioxidant compound may be present in the incubation mixture of labeled carrier and liposomes, but is most preferably incorporated within the liposome prior to incubation with the label carrier.

Liposome-encapsulated labeled protein (LELP) may also be prepared by this method in a manner analogous to that of labeled liposome preparation. Liposome-encapsulated protein having an antioxidant present within the liposome is incubated with a label carrier complex until liposome-encapsulated labeled protein is formed. It is not known to what extent the label should be membrane diffusable, although it appears that some lipophilic character is desirable and that the carrier is significantly associated with the membrane.

After incubation, excess labeled carrier and antioxidant may be washed from the LL or LELP. Since the labeling is so efficient, only a few percent of the initial radioactivity is found in the wash. In cases where the carrier and antioxidant are relatively innocuous, the washing is optional and the labeled liposomes may be used directly after incubation. This would be the case, for example, when the antioxidant is glutathione and the carrier is HMPAO. If separation is desired, centrifugation at 10–20,000 ×g may be used or, a rapid and convenient separation may be effected with a syringe pack column attached to the syringe containing the labeled liposomes. The liposomes will pass in the void volume while any free radionuclide, pertechnetate for example, would be retained on the column. In a most preferred labeling procedure for clinical use, a freeze dried preparation of $^{99m}$Tc-HMPAO is reconstituted with $^{99m}$TcO$_4^-$ and immediately incubated at room temperature with liposomes or liposome-encapsulated hemoglobin for a period as short as 5 minutes prior to use in a patient. Washing is not necessary.

In a novel aspect of the invention, it has been discovered that labeling is highly efficient when an antioxidant is encapsulated within preformed liposomes or liposome-encapsulated protein. Liposomes to be labeled may be first incubated with the antioxidant. This antioxidant/liposome mixture may then be washed, removing excess antioxidant not attached to the liposome surface. These prepared liposomes may then be incubated with the labeled carrier. Although the antioxidant may be added to the incubation mixture with liposomes or liposome-encapsulated protein, washed and then added to the label carrier, this procedure provides liposomal preparations that are less stable in vivo. This is so even though the initial labeling efficiency is quite high. Most preferably the antioxidant compound is an inorganic or organic reducing agent, for example Sn$^{+2}$ or glutathione. Compounds with free sulfhydryl appear to be suitable, for example, cysteine, although compounds of general structure RSH where R is an alkyl group or other organic moiety capable of interaction with a liposome would also be expected to work. Relatively large moieties such as proteins may also function well, particularly enzymes such as superoxide dismutase, catalase or met-hemoglobin reductase. Ascorbic acid also induced efficient binding of the label within the liposome. The mechanism of this action is not known, particularly whether or not the antioxidant agent is involved in the binding. It is possible, at least in the case of a $^{99m}$Tc-HMPAO, that presence of a reducing agent converts lipophilic $^{99m}$Tc-HMPAO to a hydrophilic form that becomes trapped inside the liposome. In any event, binding affinity of $^{99m}$Tc to liposomes or to LEH is relatively inefficient without antioxidant present. In earlier experiments, it was found that binding of the label was very efficient when LEH preparations obtained from Naval Research Laboratories (Washington, DC) were used, but labeling was poor when LEH was prepared as described in Example 1 but without glutathione or ascorbic acid. It was later found that where efficient labeling was achieved, glutathione had been present in the preparations.

Both the liposomes and the protein encapsulated within the liposome have binding affinity for the label. The precise type of interaction is not known except to say that an antioxidant such as glutathione was found to be necessary to keep the label tightly bound with the liposome, regardless of the presence of a protein.

The protein encapsulated in the liposomes is preferably hemoglobin, although other proteins binding to selected labels could be chosen. Encapsulation of substances within liposomes is well-known and techniques for encapsulation have been described (Hwang, K. J. in Liposomes from Biophysics to Therapeutics, M. J. Ostro, Ed., Marcel Dekker, Inc., New York, 1987). In particular, a method for encapsulating hemoglobin in liposomes has been described (Farmer et al., U.S. Pat. No. 4,911,929, Mar. 27, 1990). Hemoglobin appears to be preferred as the encapsulated protein because in its presence $^{99m}$Tc, presently the most widely used radionuclide in nuclear medicine, is tightly bound within the liposome (Barratt, G. M., Tuzel, N. S. and Ryman, B. E. in Liposome Technology, Vol. II, G. Gregoriadis, Ed., CRC Press, Boca Raton, 1984). Nevertheless, there may be instances in which other labels would be desired for specific studies or clinical purposes and thus a different protein might change the binding properties of the label. Certain beta-emitters, for example, might be desired and such radionuclides might bind more or less tightly in the presence of albumin or another protein. On the other hand, in certain applications, increased disassociation of the label may be desirable, as in instances where the liposome is intended to deposit the label at target organs or body areas. The label would then be dispensed at the target area. In any event, it is contemplated that the protein encapsulated may be chosen with consideration of the desired effect. Suitable proteins might include transferring, myoglobin, myosin, insulin, globulin, casein, keratin, lectin, ferritin and elastin. In addition, certain fragments or subunits of proteins might also be useful, including the β-chain of hemoglobin.

Denaturated as well as native proteins could be encapsulated within liposomes and used to bind a label. Partially denatured proteins might be useful as well, particularly if more binding sites are exposed.

Several types of labels could be used of which radionuclides would be the most useful for medical applications. Examples of beta-emitters include $^{32}$P, $^{35}$S, $^{36}$Cl, $^{24}$Na, $^{32}$K and $^{45}$Ca. Positron-emitters such as $^{68}$Ga, $^{82}$Rb, $^{22}$Na, $^{75}$Br, $^{122}$I and $^{18}$F would be useful in computerized tomographic studies. Of particular interest are the gamma-emitting radionuclides, for example, $^{24}$Na, $^{51}$Cr, $^{59}$Fe, $^{67}$Ga, $^{86}$Rb, $^{99m}$Tc, $^{111}$In, $^{125}$I and $^{195}$Pt. $^{99m}$Tc and $^{111}$In have been found particularly useful for imaging studies in human subjects.

In the incubation of liposomes or liposome-encapsulated protein with a labeled carrier, the carrier must be capable of complexing with the desired radionuclide and also diffusing through the liposomal membrane. Generally this will require a carrier that is lipophilic and also sufficiently water soluble to permit efficient transfer within the water compartment of the lipid vesicle. For the radionuclide $^{99m}Tc$, the preferred carrier is hexamethylenepropylene amine oxime. This carrier transports the metal across the bilayer membrane of the liposome and, presumably, may subsequently transfer $^{99m}Tc$ to the liposome, to the encapsulated protein or may become entrapped as the undissociated hydrophilic-converted carrier complex.

It will be recognized that a preferred carrier will depend to some extent on the lipid composition and surface charge of the liposome which can be positive, negative or neutral. A preferred carrier is HMPAO. This carrier readily crosses the membrane of negatively charged liposomes. Other carriers could be chosen on their ability to complex with the selected radionuclide and the efficiency of transport across the liposomal membrane to mediate exchange with the encapsulated capture material.

Furthermore, special ligands on the liposome surface, oligosaccharides or immunoglobulins for example, could also affect uptake of the carrier as well as targeting of the liposomes within the body. The synthesis of liposomes with charged or neutral surfaces having a wide variety of compositions is well known in the art. The selection of the appropriate liposome would require some experimentation and would depend on the carrier chosen and in turn on the radionuclide required.

Figure 7:
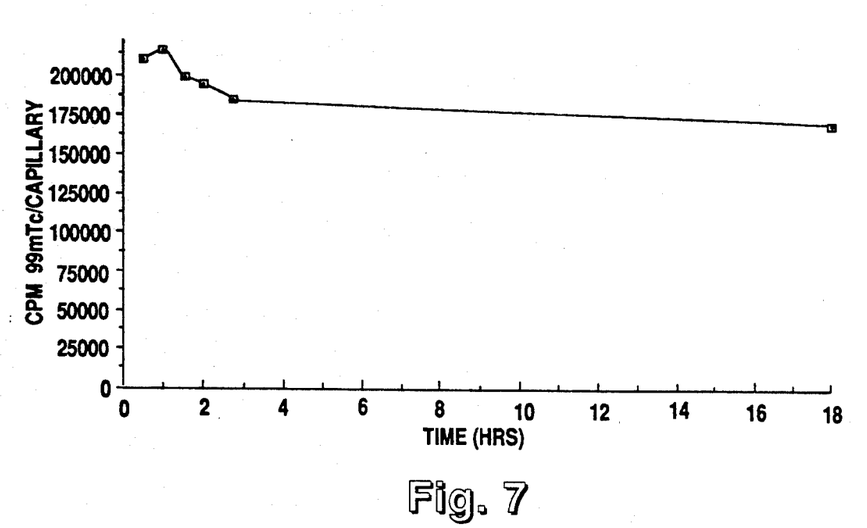
FIG. 7 is a graph of $^{99m}Tc$ radioactive counts of capillaries drawn serially after infusion of 25 milliliters of $^{99m}Tc$-labeled LEH at a concentration of 50 mg total lipid per milliliter into a 2 killgram New Zealand rabbit.
Figure 10:
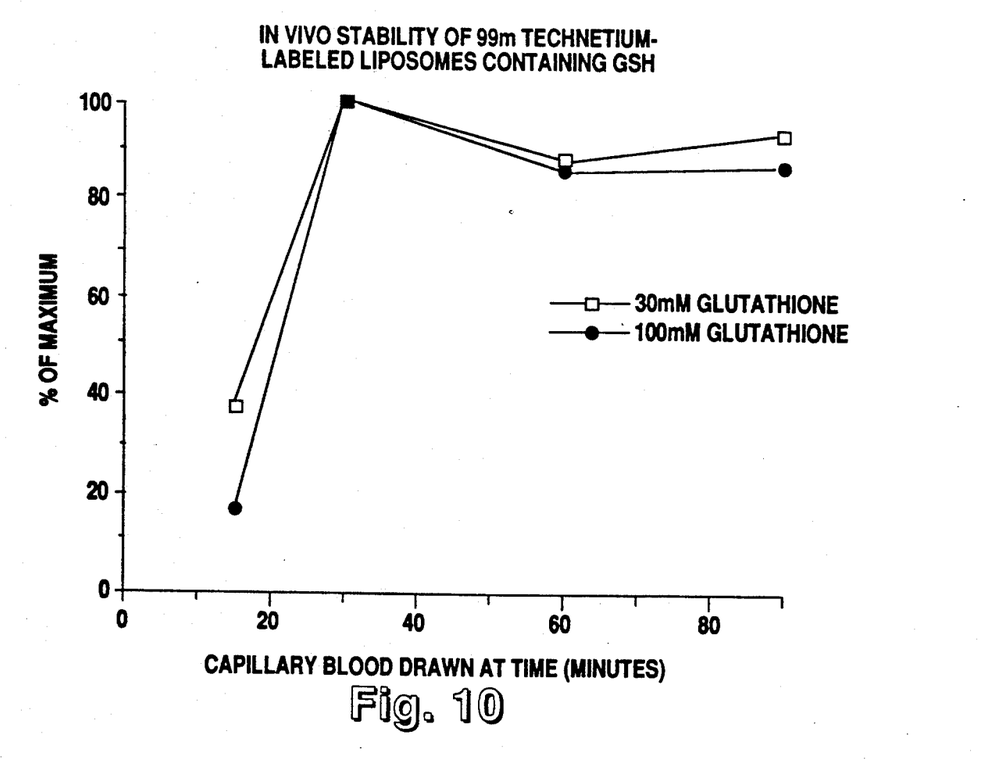
FIG. 10 shows the in vivo stability of $^{99m}Tc$-labeled liposomes prepared form liposomes containing 30 mM or 100 mM glutathione. Labeled liposomes preparations were injected into rabbits and blood samples taken at the times indicated.

The labeling efficiency of this method is greater than 90% and stability in vivo is quite high, as indicated in the examples. After more than 18 hours, 70% of the injected liposome-encapsulated $^{99m}Tc$ labelled hemoglobin was recovered in vivo from rabbit blood (FIG. 7). An in vivo experiment with $^{99m}Tc$ labelled liposomes indicated that up to 96% of the initial label remained associated with the liposomes after 1.5 hr, (FIG. 10). No other method has reported this high stability in vivo. In fact, the present invention has overcome one of the most significant disadvantages in the use of $^{99m}Tc$ as a radiolabeling agent, i.e., the apparent release of free technetium in vivo, therefore casting doubt that the radioimages are representative of intact liposomes (Barratt, G. M., Tuzel, N. S. and Ryman, B. E. in Liposome Technology, Vol. II, G. Gregoriadis, Ed., CRC Press, Boca Raton, 1984)).

The present invention also contemplates the use of $^{99m}Tc$ labelled liposomes or liposome-encapsulated labelled hemoglobin in kit form. Thus, in a preferred mode of use, freeze dried liposomes or liposome-encapsulated hemoglobin wold be incubated with a radionuclide carrier, such as $^{99m}Tc$ hexamethylenepropylene amine oxime, before administration to patients or experimental animals. Other radionuclides could be used as could other encapsulated proteins besides hemoglobin, for example albumin, as described in Example 2.

Example 4 illustrates the use of $^{99m}Tc$ labeled liposome-encapsulated hemoglobin in biodistribution studies, but it will be appreciated that appropriate carriers could be used to transfer other gamma emitters to capture agents within a liposome. For example, $^{111}In$, $^{125}I$ and $^{67}Ga$. The method could also be applied to beta- or positron emitters; for example, $^{32}P$, $^{35}S$ or, in the latter category, $^{68}Ga$ and $^{18}F$. The distribution of the label can be detected by means appropriate to the emitter. Gamma emitters are commonly detected using well established scintillation counting methods or nuclear gamma cameras. Beta emitters can be detected by radiation detection devices specific for beta particles while positron emitters are determined using various designs of a positron emission tomography apparatus.

Likewise, the general method described in the present invention would be particularly applicable to magnetic resonance imaging, simply by preparing a paramagnetically labeled liposome or liposome-encapsulated carrier molecule, administering the labeled liposome in vivo and determining the distribution of the paramagnetic label. The usual means for determining paramagnetic species is nuclear magnetic resonance detection. Bone marrow imaging has been shown particularly useful with $^{99m}Tc$ labeled liposomes which demonstrate a large amount of bone marrow uptake from the circulation several hours after administration (FIG. 12). $^{99m}Tc$ labeled liposomes having an average size of about 0.05–0.1 $\mu$ appear to be most useful for this purpose. Larger liposomes would be expected to image in different areas, for example, the lungs or other organs. Clearly, one could expect to image different regions of the body by using different size ranges of labeled liposome preparations.

In another aspect of the invention, $^{99m}Tc$ labeled LEH is used to label neutrophils. Neutrophils incubated with labeled liposomes apparently phagocytized the labeled liposomes and became labeled with $^{99m}Tc$. The 20% labeling achieved shows promise for developing a highly stable neutrophil label. This method could be used to achieve similar labeling with any phagocytized cell, for example monocytes or other cells that are capable of engulfing a labeled liposome. This could be controlled to some extent by the size and composition of the liposome employed.

DETAILED DESCRIPTION OF THE PREFERRED EMBODIMENTS

Liposome-Encapsulated Protein

As discussed above, several different proteins as well as different liposomal compositions may be used to prepare liposomes and encapsulated labeled protein. Albumin is an example of a protein that can be encapsulated by the method described in Example 1 used to encapsulate hemoglobin In a most preferred embodiment, hemoglobin is encapsulated in monolamellar negatively charged liposomes. Methods of producing liposome-encapsulated protein include a variety of methods, for example, reverse phase evaporation, homogenization and pressure extrusion. A method of producing liposome-encapsulated hemoglobin is described in Example 1. Other forms of hemoglobin can be substituted for bovine hemoglobin, including recombinant human hemoglobin. Well-known methods of encapsulation with liposomes could be employed to encapsulate proteins with special affinity for a desired label. The encapsulated protein need not be a native molecule or even the entire molecule. For example, only the β-chain of hemoglobin might be encapsulated. Examples of other proteins that could be encapsulated include transferring, myoglobin, myosin, ferritin, globulin, insulin, elastin, keratin, casein, hemoglobin fragments and other polypeptides.

Efficient binding of the label within the liposome requires the presence of a reductant, thought to act as an antioxidant, preferably glutathione which is most preferably encapsulated with the liposome-encapsulated protein before incubation with a label carrier. If glutathione is added to the liposome after the protein is encapsulated, the final labeled product is efficiently labeled but appears not to have high in vivo stability.

$^{99m}$Tc-labeled Liposomes

The discovery of an efficient labeling method for liposomes resulting in labeled liposomes that are stable in vitro and in vivo solves one of the more important problems in liposome labeling. The method is illustrated with the use of $^{99m}$Tc-labeled HMPAO as a carrier to introduce the label into a preformed liposome. Glutathione, ascorbic acid or other suitable antioxidant is most preferably encapsulated within the liposome prior to incubation with a labeled carrier to achieve efficient labeling. Possibly glutathione or other reducing agents convert the $^{99m}$Tc HMPAO complex into a more hydrophilic form that is retained inside the liposome (Ballinger, J. R., Reid, R. H. and Gulenchyn, K. Y., J. Nucl. Med., 29, 1998-2000(1988); Lang, J. J., J. Nucl. Med., 31, 1115 (1990); Ballinger, J., J. Nucl. Med., 31, 1115-1116 (1990)).

$^{99m}$Tc Carriers

The $^{99m}$Tc carrier found most preferable is an alkylenepropyleneamine oxime that complexes with $^{99m}$Tc and can be purchased as a lyophilized preparation (Ceretec ™, Amersham, Ill.). In this form, HMPAO is mixed with sterile eluate from a technetium $^{99m}$-Tc generator. The generator eluate may be adjusted to a radioactive concentration of between 0.37–1.11 GBq (10–30 mCi) in 5 ml by dilution with preservative-free, non-bacteriostatic saline prior to mixing with 0.5 mg of HMPAO. The $^{99m}$Tc complex forms almost immediately and is then incubated with liposomes containing encapsulated reductant or liposome-encapsulated hemoglobin at room temperature for 5-15 minutes. Room temperature incubation is a significant advantage over other methods of liposome labeling presently used. $^{111}$In, for example, can be retained within liposome-encapsulated nitrilotriacetic acid but the encapsulated nitrilotriacetic acid must be incubated with $^{111}$indium chloride at 60° C. for 30 minutes. Thus $^{99m}$Tc labeled liposomes prepared by the method of the present invention could be used in the assessment of in vivo distribution of new liposome drug agents that contain proteins or other heat labile drugs, whereas the heat required for the preparation of the $^{111}$In labeled liposome would denature or destroy any encapsulated heat sensitive material.

$^{99m}$Tc liposomes also have potential in assessing the effectiveness of targeting with liposomes having antibodies attached to the surface. Antibodies to infectious agents or to tumor cells would bind to the targeted areas allowing radioimaging and possible delivery of drugs to the site.

EXAMPLE 1

Preparation of Liposome-Encapsulated Hemoglobin

Liposome components are: distearoyl phosphatidylcholine (DSPC) (American Lecithin Company, Atlanta, Ga.), supplied as Phospholipid 100-H composed of 95% hydrogenated distearoyl phosphatidylcholine and up to 5% lysophosphatidylcholine; cholesterol (Calbiochem, San Diego, Calif.) at a purity of greater than 99% by TLC; and Dimyristoyl phosphatidyl DL-glycerol (DMPG) (Avanti Polar Lipids, Birmingham, Ala.) which was used without further purification. d-Alpha-tocopherol (Sigma, St. Louis, Miss.) was mixed in a 200 mg/ml solution in chloroform. All lipids were dried down from chloroform stock solutions in a mole ratio of 10:9:1 (DSPC:cholesterol:DMPG:alpha-tocopherol) and stored overnight in a vacuum desiccator to remove organic solvent. Samples were then rehydrated with solutions of trehalose (Pfanstiehl Laboratories, Waukegan, Ill.) in 30 mM phosphate buffered saline pH 7.4 and warmed in a water bath at 60° C. for one hour.

The resultant multilamellar vesicles formed from rehydration were reduced to large unilamellar vesicles (LUVs) using a high shear, high pressure apparatus (Microfluidics Corp., Boston, Mass.). The LUV's were then frozen in liquid nitrogen and lyophilized. The resultant dry sugar-lipid preparations were then hydrated with a solution of concentrated (25 g/ml) bovine hemoglobin (Hb) (Biopure Corp., Boston, Mass.) containing 30 mM or 100 mM glutathione or ascorbic acid and placed on an orbital shaker at 4° C. for 2 hours. These solutions were then run through a microfluidizer to form LEH and centrifuged to remove extravesicular hemoglobin and reducing agent (14,000×g for 1 hour). The resulting LEH was concentrated by centrifugation and stored in the refrigerator at 4° C. or shell frozen using a bench top lyophilized.

EXAMPLE 2

$^{99m}$Tc Labeling of Liposome-Encapsulated Hemoglobin

Liposome-encapsulated hemoglobin (prepared as described in Example 1 or purchased from Vestar, Inc., San Dimas, Calif. or Naval Research Laboratories, Washington, D.C.) was washed 3 times with phosphate buffered saline by centrifugation and resuspended with phosphate buffered saline to remove subcellular-sized debris and free hemoglobin. LEH containing glutathione or ascorbic acid was resuspended in PBS to yield a hematocrit value of approximately 50. $^{99m}$Tc (10 mCi) in 5 ml sterile water for injection was used to reconstitute hexamethylenepropylene amine oxime (HMPAO) supplied as a freeze dried preparation (Ceretec ™, Amersham, Arlington Heights, Ill.) for 5 min at room temperature. This mixture of $^{99m}$Tc-HMPAO complex and glutathione was then incubated with LEH (10 mg –1000 mg total lipid dose of LEH containing 2.5–300 mg intravesicular hemoglobin) for 5 minutes with intermittent swirling after which the radio-labeled LEH was washed (centrifugation at 20,000 ×g for 30 minutes) with PBS and the labeling efficiency determined (bound to pellet/total). LEH was then resuspended to a constant lipid dose for injection.

Figure 1:
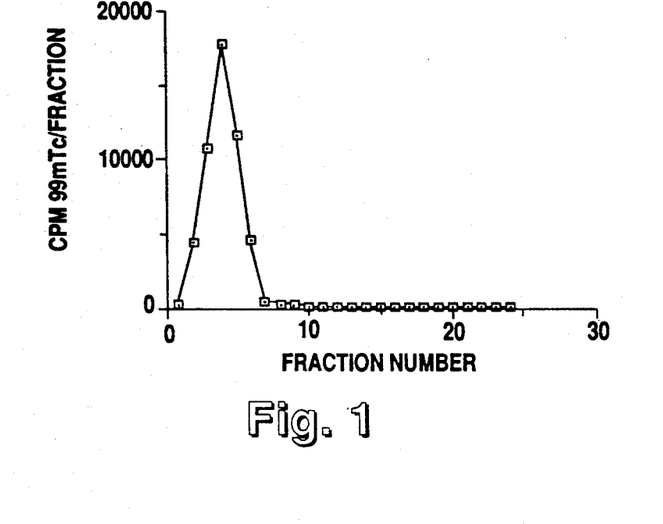
FIG. 1 is a graph showing the fractionation of liposome-encapsulated $^{99m}Tc$ labeled liposomes on a Sephadex G-200 column 70 hours after binding of the label to the encapsulated hemoglobin. All the $^{99m}Tc$ is associated with the liposomal fraction.
Figure 2:
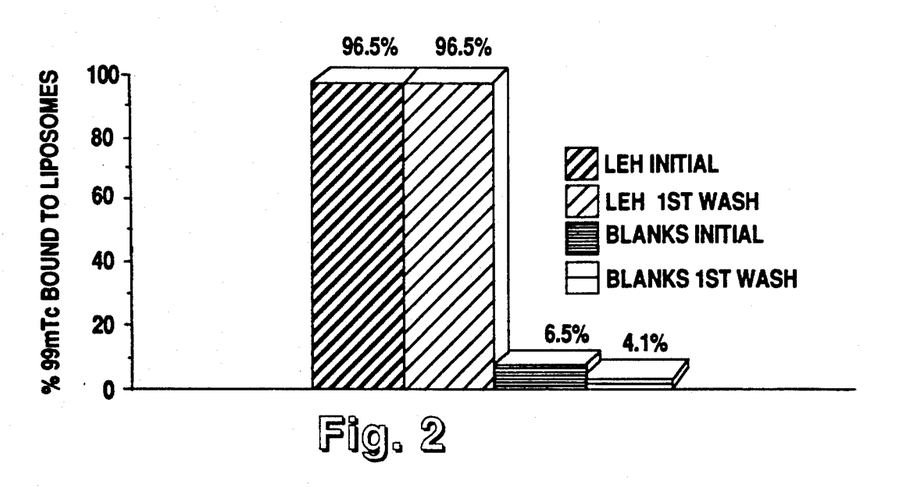
FIG. 2 shows the percent $^{99m}Tc$ binding initially to liposomes using HMPAO where LEH is liposome-encapsulated hemoglobin and blanks are liposomes without encapsulated material. There is no loss of the $^{99m}Tc$ label during the first wash.

Fractionation of $^{99m}$Tc-labeled LEH on Sephadex G-200 70 hours after binding is shown in FIG. 1. The labeled LEH eluted with the void volume. There was insignificant detection of free $^{99m}$Tc. FIG. 2 indicates that liposomes without hemoglobin (blanks) bound less than 10% of the $^{99m}$Tc added to LEH preparations. The blanks were prepared as described in Example 1 for the preparation of LEH except that during hydration no hemoglobin or glutathione were added.

Figure 3:
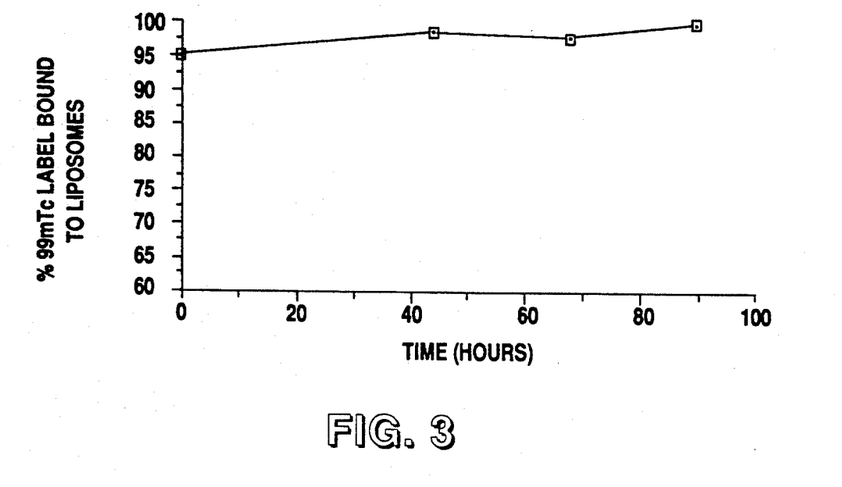
FIG. 3 shows the in vitro stability of $^{99m}Tc$ labeled liposomes in lactated Rangers solution at 2° C.
Figure 9:
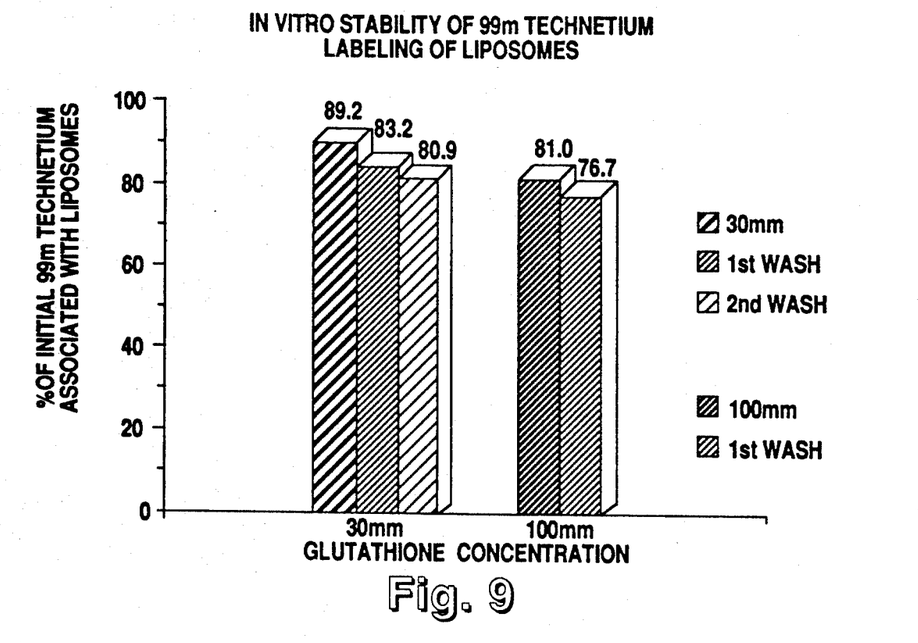
FIG. 9 shows the in vitro stability of $^{99m}Tc$-labeled liposomes prepared using liposomes encapsulating 30 mM or 100 mM glutathione.

The $^{99m}$Tc-labeled LEH exhibited excellent in vitro stability over a period of at least 90 hours storage in lactated Ringer's solution, as shown in FIG. 3 and in FIG. 9. FIG. 3 shows the stability of liposome-encapsulated labelled hemoglobin prepared from LEH purchased from Naval Research Laboratories and incubated with $^{99m}$Tc-HMPAO without the addition of glutathione (glutathione is present as a result of the particular method of preparation of LEH). FIG. 9 shows the stability of liposome-encapsulated labelled hemoglobin prepared as described above with glutathione present at a concentration of 20 mM or 100 mM.

Figure 4:
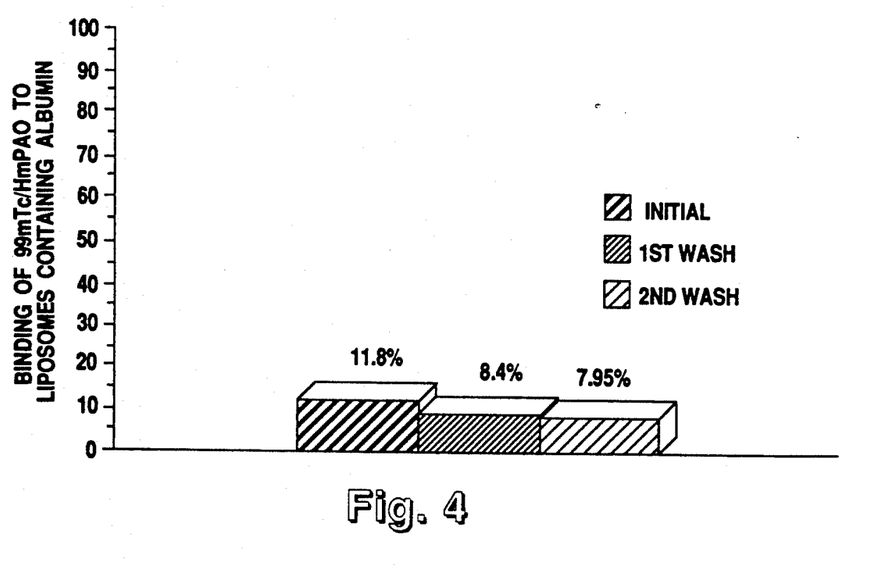
FIG. 4 shows 11.8% initial binding of $^{99m}Tc$ to liposome-encapsulate albumin.

Liposome-encapsulated albumin was prepared as described for hemoglobin except that glutathione was omitted from the incubation mixture. Approximately 12% of the label carried by the $^{99m}$Tc-HMPAO became bound to the encapsulated albumin. One-third of the label was removed after two washings with PBS (see FIG. 4).

EXAMPLE 3

$^{99m}$Tc-labeled Liposomes

Figure 11:
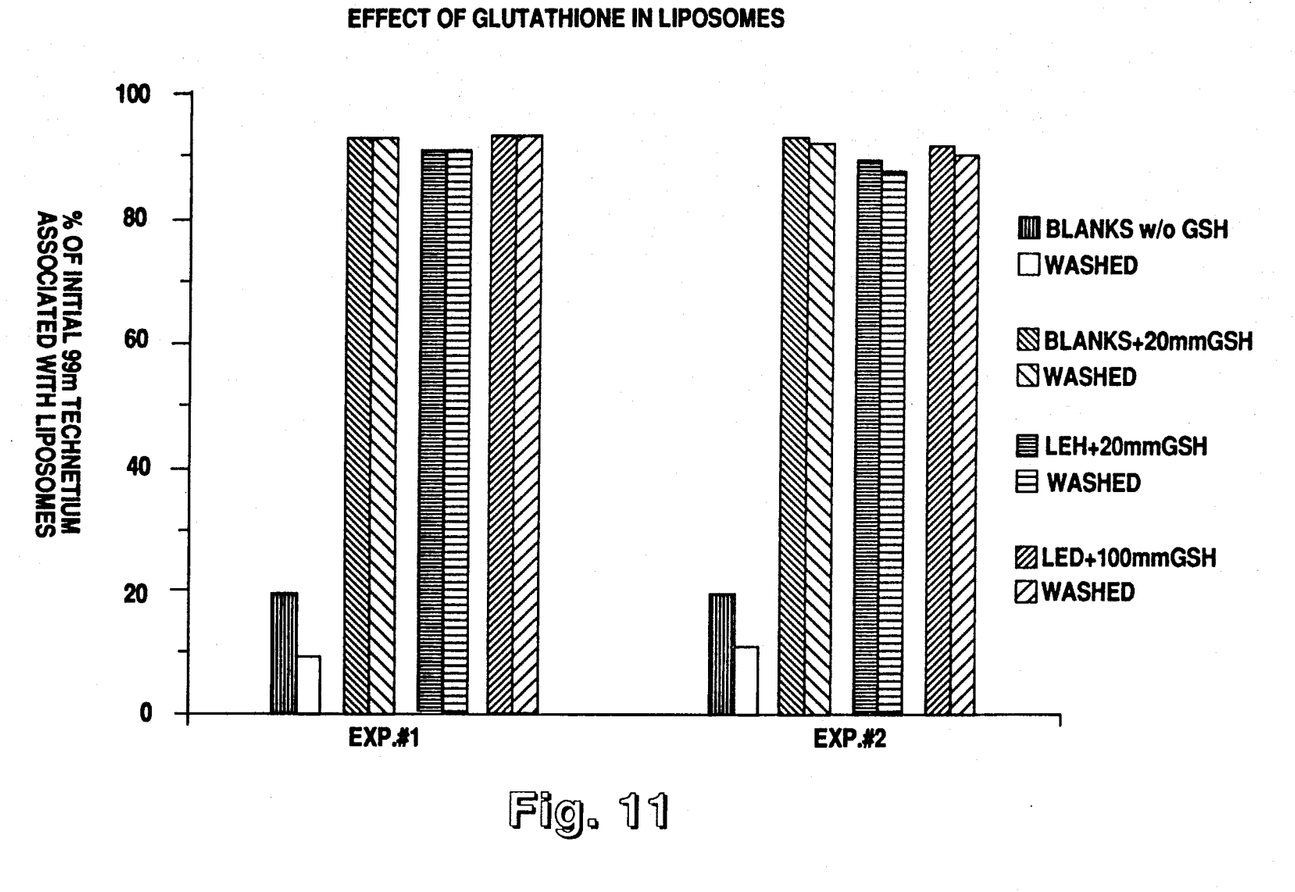
FIG. 11 is a chart comparing $^{99m}$Tc-labeling efficiency and effect of washing on blank liposomes, liposomes encapsulating 20 mM glutathione, and liposome-encapsulated hemoglobin also entrapping either 20 mM glutathione or 100 mM glutathione.
Figure 12A:
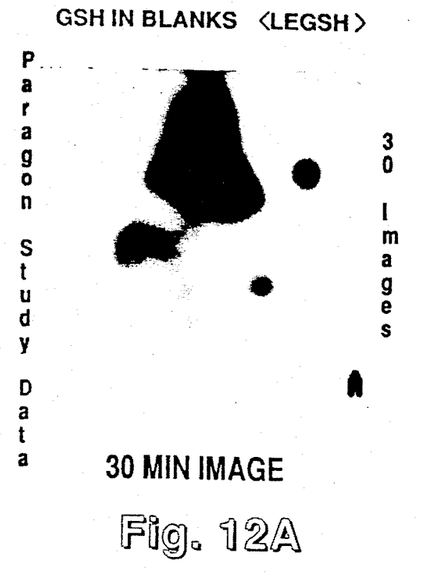
FIG. 12 is a gamma scintillation image of a rabbit after administration of $^{99m}$Tc-labeled liposomes containing glutathione. The four frames are different images of the same rabbit. The top frames show the middle body taken at 30 minutes and 90 minutes. The lower frames show the top of the body, frame C, and the lower body, frame D, images taken after 20 hours.
Figure 12B:
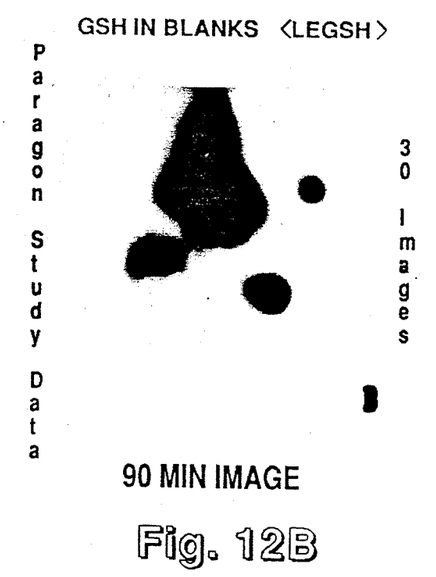
Figure 12C:
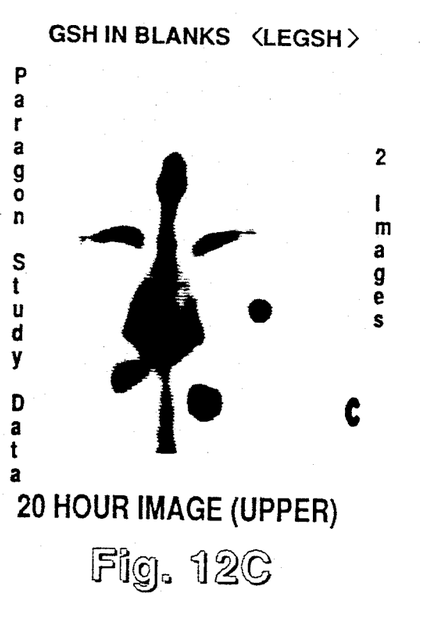
Figure 12D:
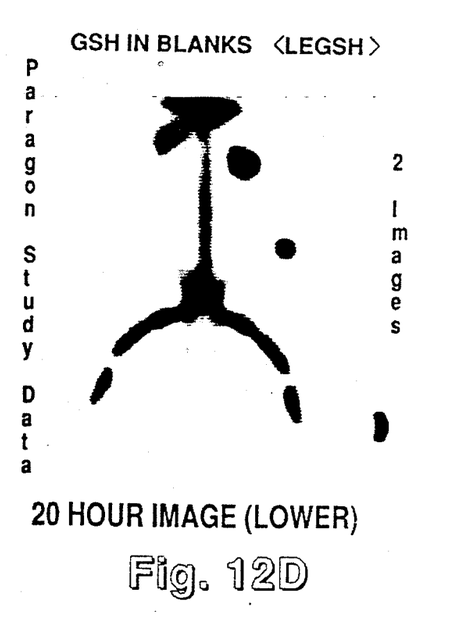

Liposomes prepared as described in Example 1 above or purchased from a commercial source (Vestar, San Dimas, Calif.) and containing 30 mM or 100 mM glutathione were incubated with $^{99m}$Tc-HMPAO. The percent of initial $^{99m}$Tc associated with the liposomes was measured before and after washing and compared with the amount of label retained in liposome-encapsulated labeled hemoglobin. The results are shown in FIG. 9 and FIG. 11. There was virtually no loss of $^{99m}$Tc label from liposomes or liposome-encapsulated hemoglobin prepared by incubating with $^{99m}$Tc-HMPAO in the presence of glutathione. Labeling efficiency was less than 20% when glutathione was absent and there was a loss of almost 50% of the label after a single wash.

In vivo stability of $^{99m}$Tc labeled liposomes was 85% and 90% respectively for liposomes incubated in the presence of 30 mM and 100 mM glutathione when tested over a period of 1.5 hr. (FIG. 10).

EXAMPLE 4

Animal Biodistribution Studies with $^{99m}$Tc-labeled LEH

Figure 5A:
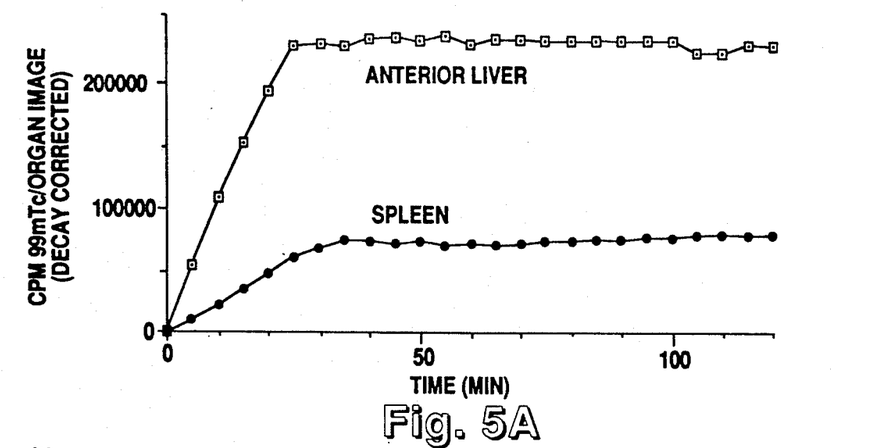
FIG. 5 shows time activity curves acquired from imaging data of the heart, liver, spleen, bladder and lung of a rabbit injected with $^{99m}Tc$ labeled LEH.
Figure 5B:
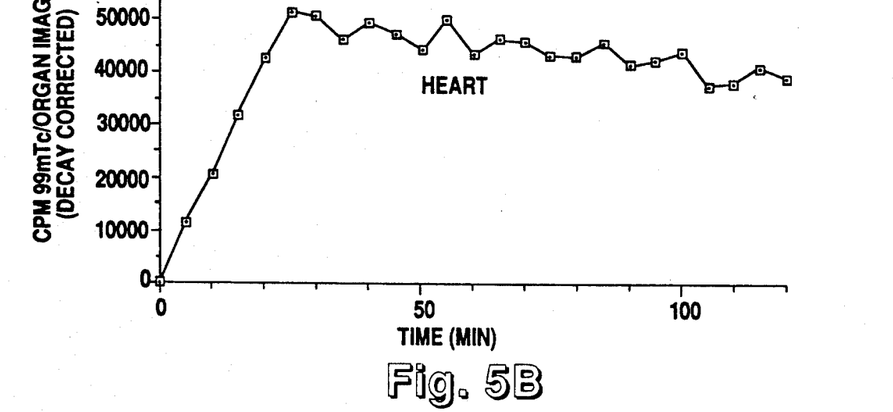
Figure 5C:
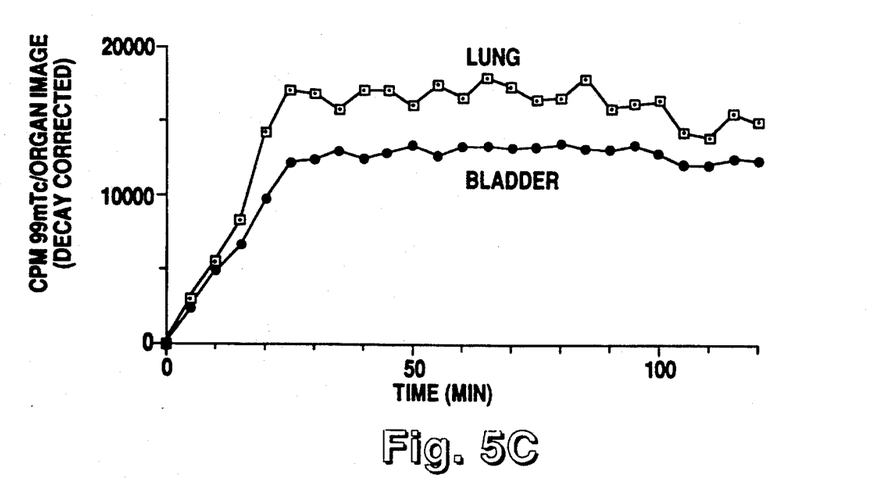
Figure 6:
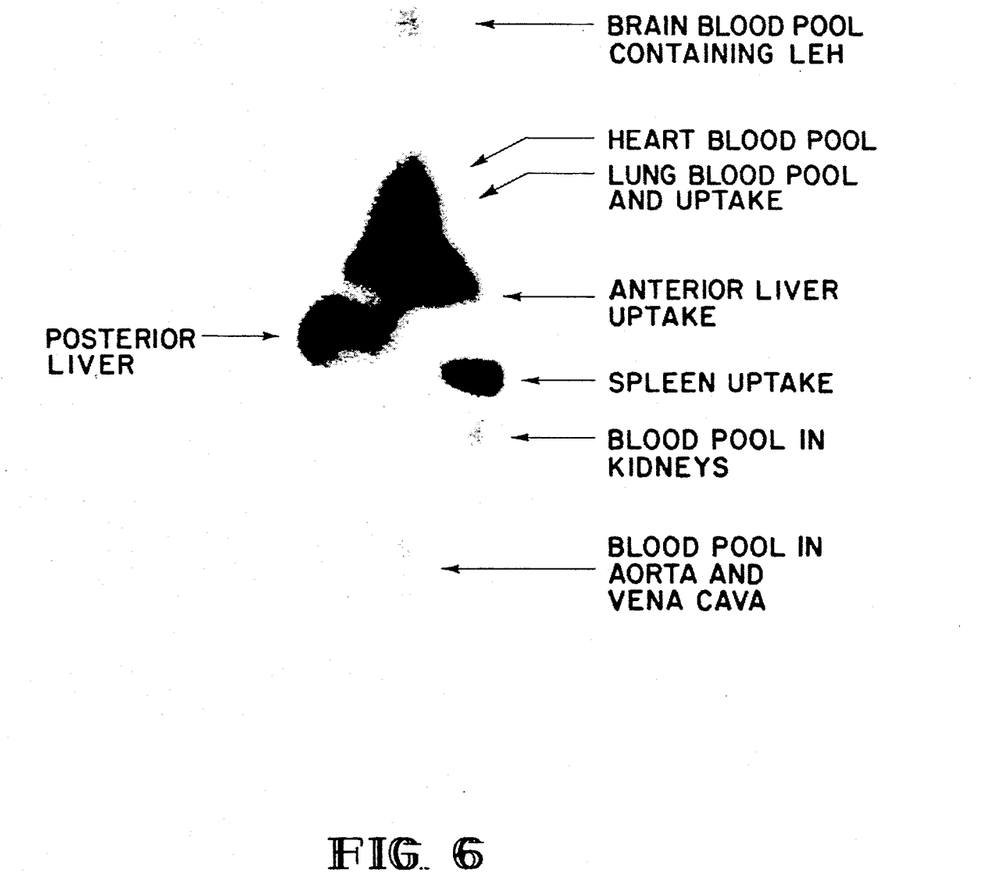
FIG. 6 shows various anatomical features seen on the image of a New Zealand rabbit infused with $^{99m}Tc$-labeled LEH acquired at 2 hours labeling.

Young adult male New Zealand white rabbits (2.5-3.0 kg) were anesthetized intramuscularly with ketamine:xylazine at 50 mg/kg:10mg/kg respectively. While anesthetized, venous and arterial access lines were secured. The rabbit was then restrained in the supine position under a low energy, parallel hole collimator of a gamma camera and imaged for $^{99m}$Tc activity at 140 Kev with a 20% window. Baseline blood samples were drawn and the metered (40 ml/kg/hr) injection of the LEH was begun. An aliquot of the injection material was reserved for lipid analysis and radioactive quantitation. Blood was then drawn at intervals to assess changes in blood chemistry, complete blood counts, the duration of LEH in the circulation and subsequent deposition and processing of the LEH by the organ systems. At 20 hours post-injection, the rabbit was sacrificed by anesthesia overdose and tissues recovered for quantitation and pathology study. Images acquired for the first two hours and at 20 hours were analyzed by drawing regions of interest around all organ systems (heart, lungs, anterior and posterior liver, spleen, kidneys, bladder and aorta) within the camera field of view. Counts in these regions of interest were calculated at 1 min interval for 20 hours and then a 20 hours. Counts were decay corrected to correct for radioactive decay. These data were entered into a MacIntosh computer for graphic demonstration of changes in biodistribution occurring with time as shown in FIG. 5. The levels of $^{99m}$Tc distribution in the rabbit heart, liver, spleen and lungs are shown in FIG. 6. FIG. 12 shows the distribution of the label concentrated in the bone marrow 20 hours after administration.

The in vivo recovery of $^{99m}$Tc-labelled LEH from rabbit blood over a period of 18 hours is shown in FIG. 7.

EXAMPLE 5

$^{99m}$Tc-Labeling of Neutrophils

Figure 8:
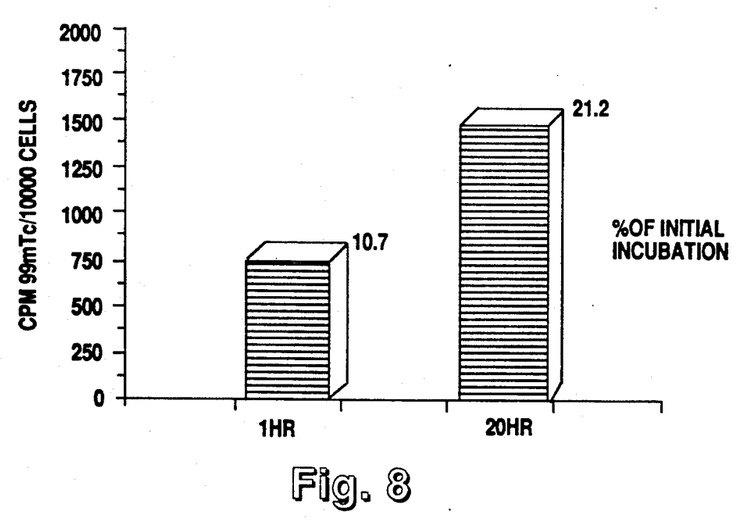
FIG. 8 shows the labeling of neutrophils incubated with $^{99m}Tc$ labeled liposome-encapsulated hemoglobin. The radioactivity labeling efficiency of the neutrophils is 10.7% after 1 hour of incubation and 21.1% after 20 hours of incubation.

Sixty ml of whole blood was drawn and diluted with 3 volumes of Hanks Buffered Salt Solution. Neutrophils were isolated with Ficol Hypaque centrifugation at 600×g for 20 minutes. Recovered neutrophils were washed ×2 with a lymphocyte maintenance medium. The neutrophils were counted and 2 separate aliquots of $10^7$ neutrophils were incubated with radiolabeled LEH for 1-20 hours at 37° C. The suspensions were counted and then centrifuged to yield a neutrophil pellet. The pellet was resuspended and washed ×2. The labeling efficiency was then determined (bound to white cell pellet/total). As shown in FIG. 8, over 20% of the initial activity was incorporated by the neutrophils after 20 hours of incubation.

EXAMPLE 6

Bone Marrow Imaging

Two rabbits were injected with $^{99m}$Tc labeled liposomes prepared as described in Example 3. Twenty hr after administration, images were taken on the whole animal using a gamma scintillation camera set at 140 KeV with a 20% window. As shown in FIG. 12, the majority of the radionuclide had left the circulation and was concentrated in the bone marrow.

The present invention has been described in terms of particular embodiments found by the inventors to comprise preferred modes of practice of the invention. It will be appreciated by those of skill in the art that in light of the in the particular embodiments exemplified without departing from the intended scope of the invention. For example, various modifications of the liposomal surfaces could be used to better target certain organs, or glutathione analogs or derivatives could be used to modify properties of the carrier without affecting the intended nature or practice of the invention. All such modifications are intended to be included within the scope of the claims.

The references cited within the text are incorporated herein by reference to the extent that they supplement, explain, provide a background for or teach methodology, techniques and/or compositions employed herein.

What is claimed is:

1. A method of preparing a radio-labelled liposome, comprising incubating the liposome with gamma-emitting radionuclide-labeled alkyleneamine oxime and an antioxidant, said incubating being for a period of time sufficient to form radio-labeled liposomes.

2. A method of preparing liposome-encapsulated radio-labelled protein, comprising incubating liposome-encapsulated protein with a gamma-emitting radionuclide-labeled alkyleneamine oxime and an antioxidant, said incubating being for a period of time sufficient to form labeled liposome-encapsulated protein.

3. The method of claim 1 or 2 wherein excess gamma-emitting radionuclide-labeled alkylene amine oxime is washed from the labeled liposomes or the liposome-encapsulated labeled protein.

4. The method of claim 1 or claim 2 wherein the antioxidant is a reductant.

5. The method of claim 1 or claim 2 wherein the antioxidant is glutathione or cysteine.

6. The method of claim 1 or claim 2 wherein the antioxidant is ascorbic acid.

7. The method of claim 1 or claim 2 wherein the antioxidant is reducing metal cation.

8. The method of claim 1 or claim 2 wherein the gamma-emitting radionuclide-labeled alkylene amine oxime comprises $^{51}$Cr, $^{59}$Fe, $^{67}$Ga, $^{86}$Rb, $^{99m}$Tc, and $^{111}$In.

9. The method of claim 1 or claim 2 wherein the gamma-emitting radionuclide-labeled alkyleneamine oxime is $^{99m}$Tc-hexamethylenepropylene amine oxime.

10. The method of claim 1 or claim 2 wherein the charge on the liposome is negative.

11. The method of claim 2 wherein the liposome-encapsulated protein is hemoglobin.

12. The method of claim 2 wherein the liposome-encapsulated protein is a $^{99m}$Tc-binding protein selected from the group consisting of albumin, transferring, myoglobin, myosin, insulin, globulin, casein, keratin, lectin, ferritin and elastin.

13. The method of claim 2 wherein the protein is at least partially denatured, said at least partially denatured protein binding a radionuclide label with greater affinity than the carrier.

14. The method of claim 2 wherein the protein is the $\beta$-chain of hemoglobin.

15. The method of claim 2 wherein the liposome-encapsulated labeled protein is liposome-encapsulated $^{99m}$Tc-hemoglobin.

16. A method of determining in vivo biodistribution, comprising
   administering to an animal an amount of radio-labelled liposome prepared in accordance with claim 1 or claim 2, said amount being sufficient for detection by radiation detection and
   determining in vivo biodistribution.

17. The method of claim 16 wherein the radio-labeled liposome comprises $^{99m}$Tc-hemoglobin.

18. The method of claim 16 wherein the radio-labeled liposome comprises $^{99m}$Tc-labeled liposome.

19. A method for labeling neutrophils, comprising the steps:
   incubating neutrophils with liposome-encapsulated $^{99m}$Tc-hemoglobin or $^{99m}$Tc-labeled liposomes for a time sufficient to form $^{99m}$Tc-labeled neutrophils; and
   separating the $^{99m}$Tc-labeled neutrophils.

20. A kit useful for preparing radiolabeled liposomes or liposome-encapsulated radiolabeled protein, comprising:
   a transporter being compartmentalized to receive one or more container means in close confinement therein;
   a first container means comprising an alkyleneamine oxide being capable of binding to a gamma-emitting radionuclide; and
   a second container means comprising liposomes encapsulating a reducing agent or liposome-encapsulated protein and reducing agent.

21. The kit of claim 20 wherein the alkyleneamine oxime, the liposomes and the liposome-encapsulated protein are lyophilized.

22. The kit of claim 20 wherein the alkyleneamine oxime is hexamethylenepropylene amine oxime or propylene amine oxime.

23. The kit of claim 20 wherein the radionuclide is $^{99m}$Tc, $^{67}$Ga or $^{111}$In.

24. The kit of claim 20 wherein the protein is hemoglobin, albumin, myoglobin, transferring or ferritin.

25. The kit of claim 20 wherein the reducing agent is glutathione or ascorbic acid.

26. A radionuclide-containing vesicle comprising $^{99m}$Tc bound to liposomes or liposome-encapsulated protein wherein a reducing agent is encapsulated with the liposomes or liposome-encapsulated protein.

27. The vesicle of claim 26 wherein the liposome-encapsulated protein is hemoglobin.

28. The vesicle of claim 26 wherein the reducing agent is glutathione or ascorbic acid.

29. A method of imaging bone marrow comprising the steps:
   administering to an animal or human the radionuclide vesicle of claim 26 in an amount sufficient for detection by radiation detection means; and
   determining distribution of the labelled vesicle after the vesicle has concentrated in the bone marrow.

30. The method of claim 29 wherein the imaging is determined about 20 hours after administration.

31. The method of claim 29 wherein the vesicles are liposomes about 0.1–0.2 $\mu$ in size.

* * * * *